(12) United States Patent
Loper

(10) Patent No.: US 6,807,885 B2
(45) Date of Patent: Oct. 26, 2004

(54) TORQUE LIMITING WRENCH FOR AN ULTRASONIC MEDICAL DEVICE

(75) Inventor: James H. Loper, Wales, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 0 days.

(21) Appl. No.: 10/342,636

(22) Filed: Jan. 15, 2003

(65) Prior Publication Data
US 2004/0134316 A1 Jul. 15, 2004

(51) Int. Cl.[7] .......................................... B25B 23/142
(52) U.S. Cl. ...................................... 81/478; 81/483
(58) Field of Search .......................... 81/467, 478, 483

(56) References Cited

U.S. PATENT DOCUMENTS

| | | | |
|---|---|---|---|
| 3,132,548 A | * | 5/1964 | Livermont .................. 81/483 |
| 3,202,021 A | * | 8/1965 | Livermont .................. 81/483 |
| 3,955,662 A | | 5/1976 | Thackston |
| 4,393,734 A | | 7/1983 | Thorn et al. |
| 4,467,678 A | * | 8/1984 | Lindholm .................. 81/483 |
| 4,535,659 A | | 8/1985 | Yang |
| 4,572,041 A | | 2/1986 | Rissmann |
| 4,655,104 A | * | 4/1987 | Blattner .................. 81/483 |
| 4,688,454 A | | 8/1987 | Scull |
| 5,108,238 A | | 4/1992 | Ewing |
| 5,152,200 A | * | 10/1992 | Kaplan .................. 81/478 |
| 5,287,775 A | | 2/1994 | Moore |
| 5,467,674 A | | 11/1995 | Thorn |
| 5,571,014 A | | 11/1996 | Gregory, Jr. et al. |
| 5,890,406 A | | 4/1999 | Thorn |
| 6,021,694 A | * | 2/2000 | Beger .................. 81/483 |
| 6,162,053 A | * | 12/2000 | Hollander .................. 81/483 |

\* cited by examiner

Primary Examiner—James G. Smith
(74) Attorney, Agent, or Firm—Palmer & Dodge, LLP; Richard B. Smith; David J. Dykeman

(57) ABSTRACT

The present invention provides an apparatus and method for a torque limiting wrench used for applying a torque to a medical device to prevent damage to the medical device by providing a predetermined torque limit to indicate when the predetermined torque is reached. The torque limiting wrench comprises a gripping mechanism for engaging a medical device, a handle extending from the gripping mechanism and a torque limiting assembly contained within a length of the handle. A predetermined torque is set by the torque limiting assembly to provide an indicator to prevent damage to the acoustic characteristics of the medical device. The torque limiting wrench comprises a material that can undergo a sterilization process.

43 Claims, 12 Drawing Sheets

TORQUE LIMITING WRENCH FOR AN ULTRASONIC MEDICAL DEVICE

RELATED APPLICATIONS

None.

FIELD OF THE INVENTION

The present invention relates to a torque limiting wrench, and more particularly to an apparatus and method of transferring an applied torque from a wrench to an ultrasonic medical device wherein the wrench is set to a predetermined torque to allow a user to supply an appropriate amount of torque to the ultrasonic medical device to not damage the medical device.

BACKGROUND OF THE INVENTION

Torque limiting wrenches are used in many different applications of adjusting various components including, but not limited to, bolts, nuts and fasteners. Torque limiting wrenches are used for applications where transmission of a consistent level of torque is needed. A consistent level of torque is important for a number of reasons. A torque limiting wrench assures that components are fully tightened. If a component is not fully tightened, the component can become loose wherein the component can become unengaged. A component that is not fully tightened can further adversely affect the functionality of the device as a whole. In addition, a torque limiting wrench prevents overtorqueing a component. Overtorqueing a component can lead to localized overstressing of the component, which can result in damage to various parts of the component. For example, overtorqueing a component that has threads can lead to damaged threads or stripped threads.

The efficiency of a torque limiting wrench is affected by the mechanics of the torque limiting wrench. It is important in the design of a torque limiting wrench that the mechanics are designed so that the functionality is not affected by the number of uses, environment in which the torque limiting wrench will be used or environments in which the torque limiting wrench will be subjected to. Torque limiting wrenches used with medical devices are often required to be subjected to a sterilization process. For many applications, the sterilization process comprises an autoclave. The sterilization process subjects the components of the torque limiting wrench to increased wear and tear. The integrity of any lubricants or parts that require lubricants may be compromised in the sterilization process.

Medical devices are often delicate, precise and sensitive instruments. The functionality and reliability of a medical device may be dependent upon all components of the medical device being fastened properly, all components of the medical device being tightened to the correct torque limit, and the surface conditions being devoid of scratches, burrs, nicks or other surface residue. These conditions allow the medical device to be tuned properly.

Use of a torque limiting wrench often requires that a part of the torque limiting wrench engage a component of the device that is to be tightened. In other cases, there is not direct contact between a part of the torque limiting wrench and the device that is to be tightened. In the case where a part of the torque limiting wrench physically contacts a component of the device that is to be tightened, the contacting part of the torque limiting wrench must not alter the surface conditions of the device that is being tightened. Some altering of the surface conditions of the device being tightened include, but are not limited to, scratching, nicking, burring or leaving residue on the surface of the device being tightened.

There have been several attempts in the prior art for providing a device that prevents overtightening of components. Many prior art devices are complicated, bulky and can adversely affect the components that are being tightened. Many of the prior art devices utilize external power sources and various lubricants in the mechanics and require that the torque limiting wrench move over the component to be tightened. Some prior art devices utilize external mechanisms to physically contact the component that is being tightened.

U.S. Pat. No. 3,955,662 to Thackston discloses a power tool having an adjustable torque-limiting coupling and a shut off means. The torque responsive coupling operates in response to a selected torque load to stop the driving connection between a driving member and a driven member. The power tool has a unit that couples a driving shaft to a driven shaft by means of a coil of variable cross section, with the release force a direct function of the cross sectional area of the coil that overlies the interface between the driving and driven members. The power tool uses a fluid motor with materials that would not be able to withstand a sterilization process that includes an autoclave. The power tool is expensive, complicated, large, requires an air power supply and has a fluid in the motor. It can be costly, difficult and cumbersome to provide pneumatic lines to environments where the power tool is to be used. The power tool requires that the power tool be moved over the component to be tightened and can alter the surface conditions of the component to be tightened. Altering the surface conditions of the component to be tightened can damage the component and adversely affect the functionality of the component. Since medical devices are sensitive instruments that require precise and accurate tightening and must be devoid of scratches, burrs, nicks or other surface residue, the power tool could not be used to tighten a medical device. Therefore, a need remains in the art for an apparatus and method of transmitting torque of a predetermined value to a component, the apparatus and method of which is compact, not complicated, does not require external power sources, moves on and off of the device to be tightened, comprises materials that will withstand an autoclave operation, does not damage and/or affect the device to be tightened and can be used on a medical device.

U.S. Pat. No. 5,467,674 to Thorn discloses a combined part marking and force limiting device. The Thorn device has a marking mechanism that marks a part when the part has been manipulated to a desired torque level. The Thorn mechanism includes a force applying handle, a housing pivotally mounted to the handle and a part-marking mechanism mounted within the housing. The force applying handle moves a linkage arm, which moves a pivotable cam to allow for the part marking mechanism to mark the part. The Thorn device is complex and uses a complicated method of tightening the component. The use of a part marking mechanism to physically contact a part and apply a liquid mark to a part can lead to undesirable effects of the surface of the part being manipulated and may affect the functionality of the part. Since medical devices are sensitive instruments that require precise, accurate tightening and must be devoid of scratches, burrs, deformations, nicks or other surface residue, the Thorn device could not be used to tighten a medical device. The Thorn device requires that the wrench be moved over the component to be tightened. Often times it is impossible or inconvenient to move a wrench over the component to be tightened. Therefore, a need remains in the art for an apparatus and method of transmitting torque of a predetermined value to a component that is simple, compact, moves on and off of the device to be tightened, does not leave a residue on a part to be tightened, does not damage and/or affect the functionality of the part to be tightened and can be used on a medical device.

U.S. Pat. No. 4,572,041 to Rissmann discloses a wrench wherein the force is limited to a set value. The Rissmann wrench has an input member and an output member coupled to each other, with the coupling formed by a collar on the input member with a plurality of axially directed, circumferentially disposed catches and a plurality of spring rods associated with each catch. The spring rods are bent outwardly by the flanks of the catches and out of the range of the catches once a force is reached. The Rissmann wrench has a head comprised of a hollow hexagonal member which receives the hexagonal head of the element to be tightened. The Rissmann wrench comprises catches and spring rods and the interactions of the catches and spring rods in the torqueing process of a component to determine the targeted torque value. The Rissmann device is complex and uses a complicated method of providing for a predetermined torque. The Rissmann device requires that the device be moved over the component to be tightened and can alter the surface conditions of the component to be tightened. Altering the surface conditions of the component to be tightened can damage the component and adversely affect the functionality of the component. Since medical devices are sensitive instruments that require precise, accurate tightening and must be devoid of scratches, burrs, deformations, nicks or other surface residue, the Rissmann device could not be used to tighten a medical device. Therefore, a need remains in the art for a simple, compact apparatus and method of transmitting torque of a predetermined value to a component that includes moving the device over a component to be tightened that will not alter the surface conditions of the component, will not damage the component to be tightened and can be used on a medical device.

As discussed above, the prior art devices and methods of transmitting torque of a predetermined value to a device are bulky, complex and unreliable. The prior art devices require that the device be positioned over the part to be tightened and leave a residue on the surface of the part to be tightened that can affect the functionality of the part. The prior art devices can damage the part to be tightened. Therefore, there is a need in the art for an apparatus and method of transmitting torque of a predetermined value that is simple, compact, reliable, capable of being positioned on and off of a part to be tightened, does not alter the surface conditions of the part to be tightened, does not damage the part to be tightened, does not affect the functionality of the part to be tightened and can be used on a medical device.

SUMMARY OF THE INVENTION

The present invention is an apparatus and method of transferring an applied torque from a torque limiting wrench to an ultrasonic medical device wherein the torque limiting wrench is set to a predetermined torque. The torque limiting wrench is set to a predetermined torque to provide a plurality of indicators which indicate the predetermined torque has been reached in order to prevent damage to the medical device.

The present invention is a torque limiting wrench comprising a gripping mechanism for engaging a medical device, a handle extending from the gripping mechanism and a torque limiting assembly contained within a length of the handle wherein the torque limiting wrench transfers a predetermined torque to a medical device. The gripping mechanism comprises a pair of wrench flats that engage onto the medical device at a predetermined location and transfer a force applied to the handle of the torque limiting wrench to the medical device.

The present invention is a torque limiting wrench designed to not affect the acoustic characteristics of an ultrasonic medical device. The torque limiting wrench comprises a material that can undergo a sterilization process. A sterilization process can include an autoclave operation. The torque limiting wrench comprises a gripping mechanism comprised of a pair of wrench flats that engage the ultrasonic medical device at a predetermined location. The gripping mechanism comprises a material that will not damage the surface conditions of the ultrasonic medical device.

The present invention is a method of transferring a torque from a torque limiting wrench to a medical device wherein a torque larger than a predetermined torque does not damage the medical device. The method of transferring the torque from the torque limiting wrench to the medical device comprises setting a predetermined torque on the torque limiting wrench using an adjuster, engaging a pair of wrench flats of a gripping mechanism to the medical device and applying a force from a handle of the torque limiting wrench to the medical device using the gripping mechanism. The torque limiting wrench produces a plurality of indicators to indicate when the predetermined torque is reached.

The present invention is a torque limiting wrench for applying a torque to a medical device while preserving the acoustic properties of the medical device by providing a predetermined torque limit of the torque limiting wrench to indicate when the predetermined torque is reached. The present invention provides an apparatus and method of transmitting torque of a predetermined value to a medical device that is simple, compact, reliable, capable of being positioned on and off of the medical device, does not alter the surface conditions of the medical device, and does not damage the medical device or affect the functionality of the medical device.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of the present invention.

DETAILED DESCRIPTION

The following terms and definitions are used herein:

"Torque," as used herein, refers to a force applied to a component that rotates or turns the component. Torque is a measure of how much a force acting on a component causes that component to turn or rotate. Torque is the product of the magnitude of the force and the approximately perpendicular distance from the force to the axis of rotation of the component.

"Torque limiting assembly," as used herein, refers to a group of components of a torque limiting wrench including, but not limited to, a cap, a body, an adjuster, a pin, a bushing, a ball, a ball seat and a spring. The torque limiting assembly limits the amount of predetermined torque applied by a torque limiting wrench.

"Medical device," as used herein, refers to an instrument that is used to treat a medical condition. A medical device is a sensitive instrument that requires precision and reliability in the treatment of various diseases. A medical device includes, but is not limited to, a probe that utilizes energy (e.g., ultrasonic energy) with the ability to ablate biological material.

Figure 1:
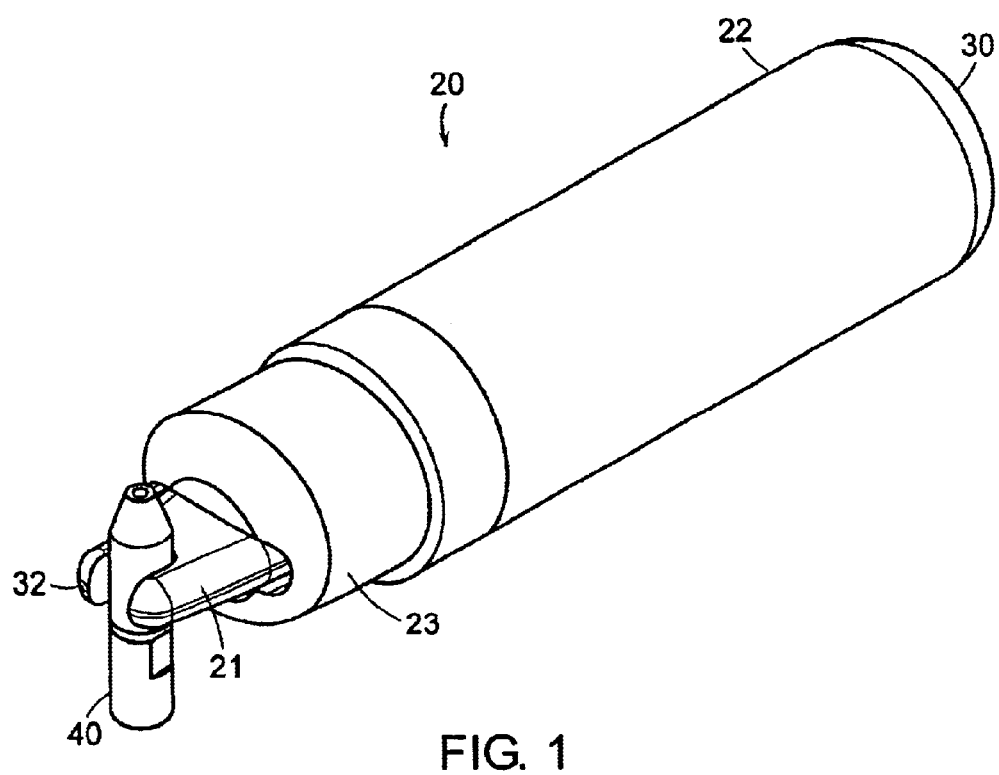
FIG. 1 shows a perspective view of a torque limiting wrench of the present invention engaging a medical device.

A perspective view of a torque limiting wrench 20 engaging a medical device 40 is illustrated generally in FIG. 1. The torque limiting wrench 20 includes a gripping mechanism 21, a handle 22, a cap 23, and the torque limiting wrench 20 has a proximal end 30 and a distal end 32. FIG. 1 illustrates the gripping mechanism 21 for engaging the medical device 40, the handle 22 extending from the gripping mechanism 21 and the cap 23 contained within a length of the handle 22. In a preferred embodiment of the present invention, the gripping mechanism 21 engages the medical device 40.

Figure 2A:
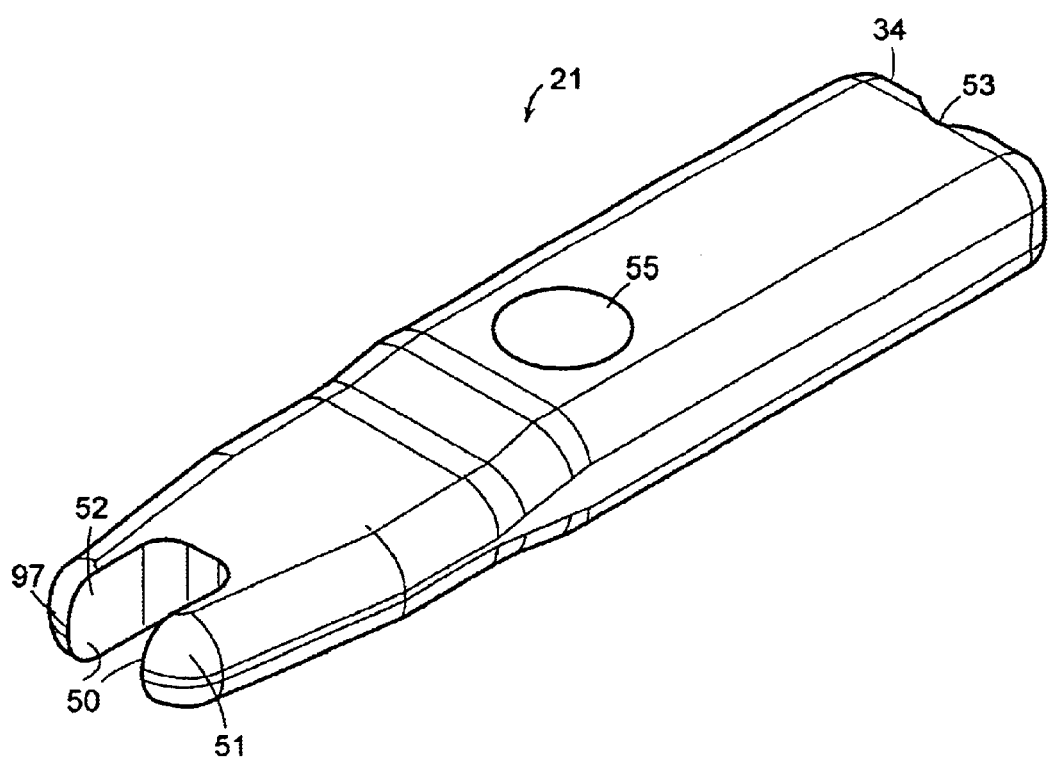
FIG. 2A shows a perspective view of a gripping mechanism of a torque limiting wrench of the present invention as seen from a distal end.

FIG. 2A shows a perspective view of the gripping mechanism 21 of the torque limiting wrench 20 of the present invention. The gripping mechanism 21 comprises a pair of wrench flats 50 with a first jaw 51 and a second jaw 52 at a distal end 97 of the gripping mechanism 21, a detent 53 at a proximal end 34 of the gripping mechanism 21 and a gripping mechanism opening 55 at a predetermined position between the distal end 97 and the proximal end 34 of the gripping mechanism 21.

The pair of wrench flats 50 includes a first jaw 51 and a second jaw 52 that engage the medical device 40 at a predetermined location. A distance between the first jaw 51 and second jaw 52 is designed to fit onto the medical device 40 at the predetermined location. In a preferred embodiment of the present invention, the first jaw 51 and the second jaw 52 fit around at least a portion of the medical device 40 at a predetermined location of the medical device 40. In a preferred embodiment of the present invention, the pair of wrench flats 50 contact a predetermined location of the medical device 40. In another embodiment of the present invention, the pair of wrench flats 50 does not contact the predetermined location of the medical device 40. The pair of wrench flats 50 with the first jaw 51 and second jaw 52 are designed to prevent damage to the medical device 40.

The gripping mechanism 21 comprises a material that will not alter the surface conditions of the gripping mechanism 21 or the medical device 40 when transferring torque from the pair of wrench flats 50 to the medical device 40 to adversely affect the surface conditions. Adverse surface condition effects include, but are not limited to, burring, scratching, deforming, nicking, leaving residual contaminants and similar effects. In a preferred embodiment of the present invention, the gripping mechanism 21 comprises a non-corrosive material. Those skilled in the art will recognize many other adverse surface condition effects are within the spirit and scope of the present invention.

In a preferred embodiment of the present invention, the detent 53 is conical. In other embodiments of the present invention, the detent 53 is square, rectangular, triangular, oval and similar shapes. Those skilled in the art will recognize the detent 53 can be of many other shapes and be within the spirit and scope of the present invention.

In a preferred embodiment of the present invention, the gripping mechanism opening 55 has an approximately circular cross section. In other embodiments of the present invention, the gripping mechanism opening 55 has a cross section that is square, rectangular, triangular, oval and similar shapes. Those skilled in the art will recognize the gripping mechanism opening 55 can be of many other shapes and be within the spirit and scope of the present invention.

In a preferred embodiment of the present invention, the gripping mechanism 21 comprises stainless steel. Stainless steel is an iron alloy with a minimum of approximately 10% chromium. Additional alloying elements are added to enhance the structure and change properties including, but not limited to, formability, strength and toughness. Alloying elements include, but are not limited to, nickel, molybdenum, titanium, copper, carbon and nitrogen. Stainless steel is corrosion resistant, is easily maintained and maintains its strength at high temperatures. Those skilled in the art will recognize there are many other materials that can be used that are within the spirit and scope of the present invention.

Figure 2B:
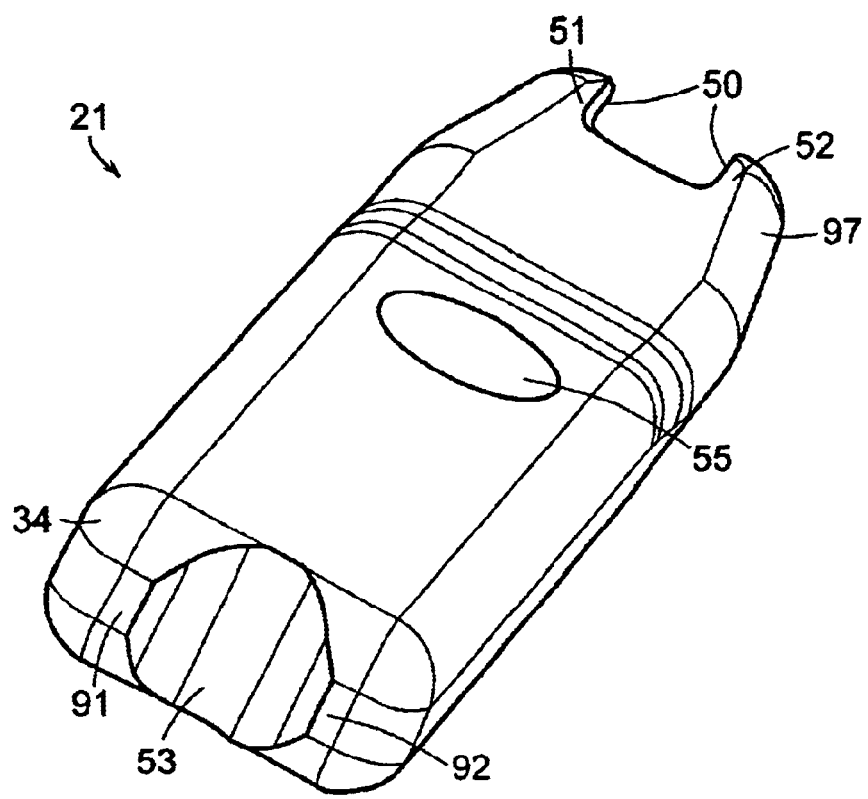
FIG. 2B shows a perspective view of the gripping mechanism of a torque limiting wrench of the present invention as seen from a proximal end.

FIG. 2B shows a perspective view of the gripping mechanism 21 as seen from the proximal end 34. In a preferred embodiment of the present invention, the proximal end 34 comprises the detent 53 and a first endface 91 and a second endface 92. In a preferred embodiment of the present invention, the gripping mechanism 21 comprises a pair of wrench flats 50 with a first jaw 51 and a second jaw 52 at a distal end 97 of the gripping mechanism 21 and a gripping mechanism opening 55 at a predetermined position between the distal end 97 and proximal end 34 of the gripping mechanism 21.

Figure 3A:
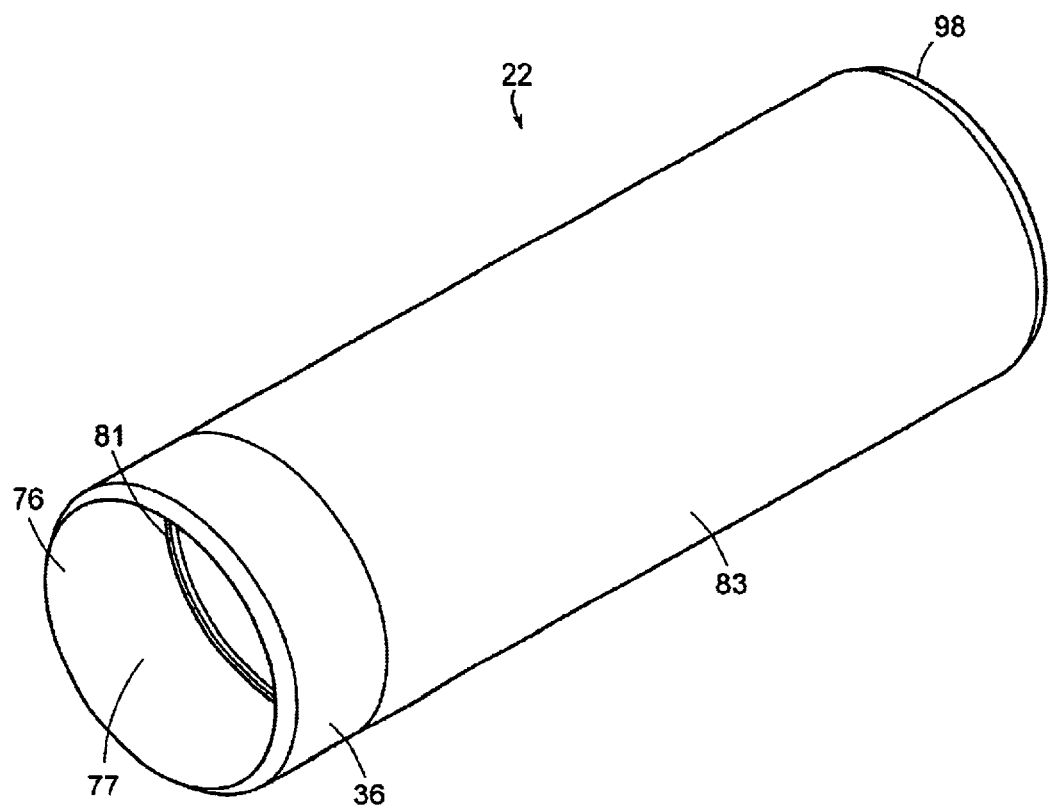
FIG. 3A shows a perspective view of a handle of a torque limiting wrench of the present invention as seen from a distal end.

FIG. 3A shows a perspective view of the handle 22 of the torque limiting wrench 20 of the present invention. In a preferred embodiment of the present invention, the handle 22 comprises a proximal end 98 and a distal end 36. At the distal end 36, there is an approximately circular opening 76 of the handle 22. On an inside surface 77 of the handle 22, a handle fastener 81 allows the handle 22 to engage to the cap 23. In a preferred embodiment of the present invention, the handle 22 comprises a section 83 of a predetermined length that has a surface finish that allows a user to grip the handle 22 in a manner that reduces the risk of the torque limiting wrench 20 slipping during application of a force to the handle 22.

In a preferred embodiment of the present invention, the handle 22 comprises anodized aluminum. In another embodiment of the present invention, the handle 22 comprises an anodized aluminum alloy. Aluminum is a light, nontoxic, nonmagnetic metal that is used in applications where a strong, light, durable and easily constructed material is needed. Anodizing is an electrochemical process that thickens and toughens the naturally occurring protective oxide. Anodizing provides durability to provide the material with long life, color stability that provides good stability to ultraviolet rays, and a coating that will not chip or peel. Anodizing is a safe process that results in a finish that is chemically stable, non-toxic, and will not decompose. Anodizing provides a finish that is heat resistant to the melting point of aluminum. Those skilled in the art recognize that the handle 22 can be made of many other materials and be within the spirit and scope of the present invention.

In a preferred embodiment of the present invention, the handle fastener 81 comprises a plurality of threads. Other handle fasteners 81 that could be used for engaging the handle 22 to the cap 23 include, but are not limited to, adhesives, glues, rivets, blind fasteners, mechanical snaps and other mechanical fasteners. Those skilled in the art will recognize that other methods of engaging the handle 22 to the cap 23 are known in the art and would be within the spirit and scope of the present invention.

Figure 3B:
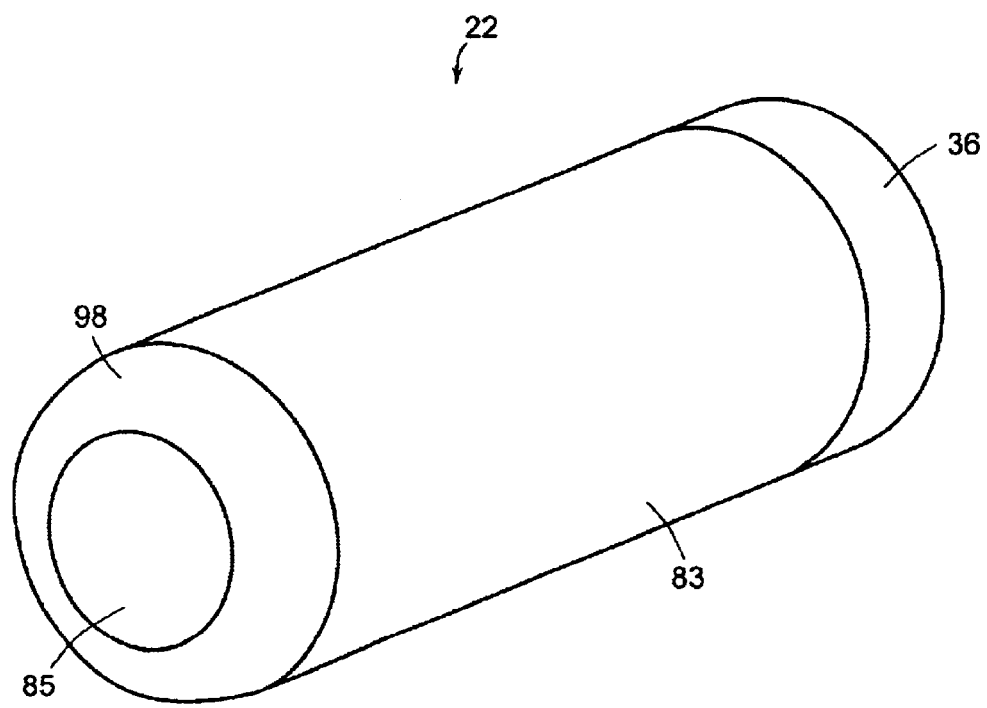
FIG. 3B shows a perspective view of the handle of a torque limiting wrench of the present invention as seen from a proximal end.

FIG. 3B shows a perspective view of the handle 22 of the present invention. In a preferred embodiment of the present invention, there is a handle opening 85 at the proximal end 98 of the handle 22. The handle opening 85 allows for an adjuster head (shown as 64 in FIG. 4) to move from an axial location within a section of the handle 22 to an axial location outside of the proximal end 98 of the handle 22. The handle 22 comprises a distal end 36 and a section 83 of a predetermined length that has a surface finish that allows a user to grip the handle 22 in a manner that reduces the risk of the torque limiting wrench 20 slipping during application of a force to the handle 22.

In a preferred embodiment of the present invention, the handle opening 85 is approximately circular. In other embodiments of the present invention, the handle opening 85 has a cross section that is square, rectangular, hexagonal, triangular, oval or similar shapes. Those skilled in the art will recognize the handle opening 85 can be of many other shapes and be within the spirit and scope of the present invention.

Figure 4:
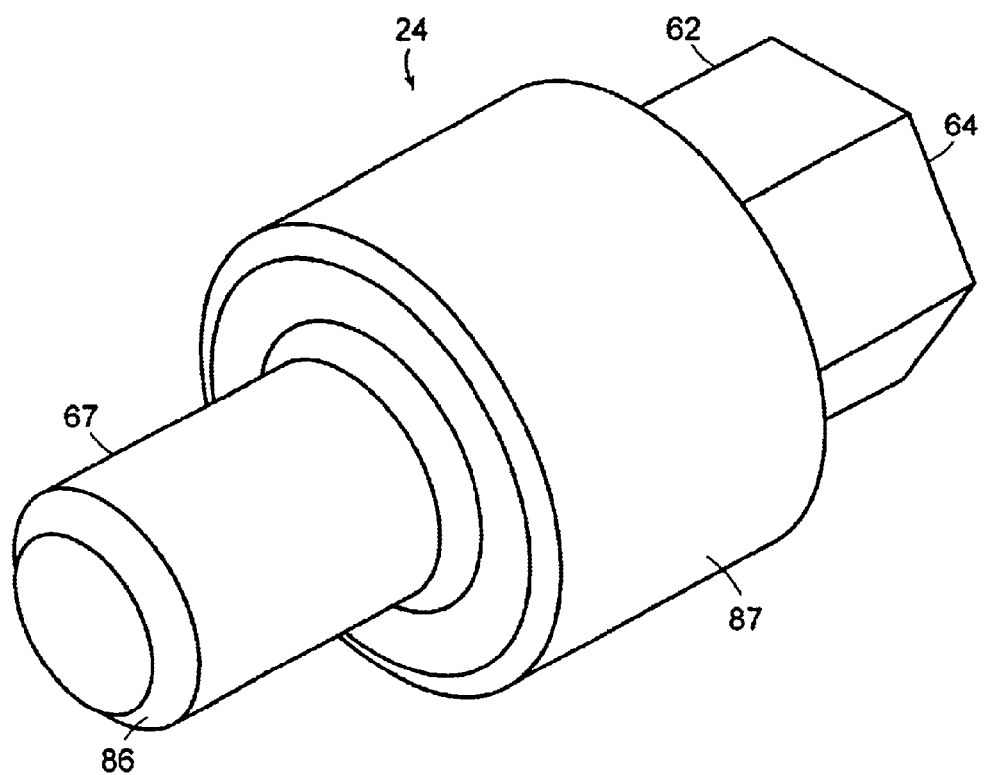
FIG. 4 shows a perspective view of an adjuster of a torque limiting wrench of the present invention.

FIG. 4 shows the adjuster 24 of the torque limiting wrench 20 of the present invention. The adjuster 24 is a component of the torque limiting assembly. The adjuster 24 comprises a proximal end 62 with an adjuster head 64 and a distal end 66 with a boss 67. The boss 67 refers to a section of the adjuster 24 that comprises a length that allows a spring (shown as 27 in FIG. 9) to fit around along a length of a longitudinal axis of the boss 67. The boss 67 comprises a cross section that allows a spring (shown as 27 in FIG. 9) to fit over a length of the boss 67. The adjuster 24 comprises an adjuster fastener 87 that is used to engage the adjuster 24 to a body (shown as 25 in FIG. 5A) at a position between the proximal end 62 and the distal end 66 of the adjuster 24.

In a preferred embodiment of the present invention, the adjuster head 64 has a hexagonal cross section. In other embodiments of the present invention, the adjuster head 64 has a cross section that is circular, square, rectangular, triangular or oval. In addition, the adjuster head 64 may further comprise an X shaped indentation, a line shaped indentation and similar indentations that allow adjustment tools known in the art to engage to the adjuster head 64. Those skilled in the art will recognize the adjuster head 64 can have many other cross sections and indentations and be within the spirit and scope of the present invention.

Adjustment tools known in the art include, but are not limited to, any type of screwdriver (i.e., standard tip, phillips tip, torx tip, cabinet tip, square tip, pozidriv tip, multi-bit), allen wrenches, hexagonal head wrenches, ratchets, pliers, nut drivers, socket wrenches, and similar adjustment tools. Those skilled in the art will recognize there are other adjustment tools that can be used to engage the adjuster head 64 are within the spirit and scope of the present invention.

Figure 5A:
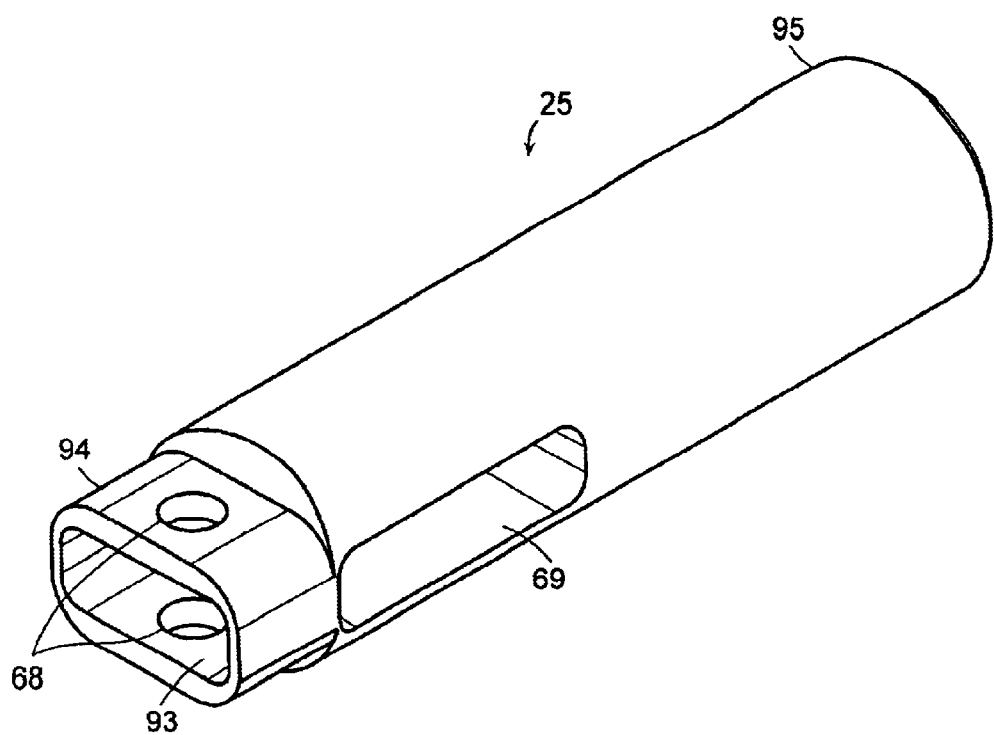
FIG. 5A shows a perspective view of a body of a torque limiting wrench of the present invention as seen from a distal end.

In a preferred embodiment of the present invention, the adjuster fastener 87 comprises a plurality of threads for engaging the adjuster 24 to the body (shown as 25 in FIG. 5A). Other adjuster fasteners 87 that could be used for engaging the adjuster 24 to the body 25 include, but are not limited to, adhesives, glues, rivets, blind fasteners, mechanical snaps and other mechanical fasteners. Those skilled in the art will recognize that other methods of engaging the adjuster 24 to the body are known in the art and would be within the spirit and scope of the present invention.

In a preferred embodiment of the present invention, the boss 67 comprises a cross section that is approximately circular. In other embodiments of the present invention, the boss 67 has a cross section that is square, rectangular, triangular, oval or similar shapes. Those skilled in the art will recognize the boss 67 can be of many other shapes and be within the spirit and scope of the present invention.

In a preferred embodiment of the present invention, the adjuster 24 comprises anodized aluminum. In another embodiment of the present invention, the adjuster 24 comprises an anodized aluminum alloy. Those skilled in the art will recognize the adjuster 24 can be made of many other materials and be within the spirit and scope of the present invention.

FIG. 5A shows a perspective view of the body 25 of the torque limiting wrench 20 of the present invention. The body 25 is a component of the torque limiting assembly. In a preferred embodiment of the present invention, the body 25 comprises a plurality of body openings 68 wherein a pin (shown as 29 in FIG. 9) is inserted, a side body opening 69 at a predetermined location along the side of the body 25 and a front body opening 93 at a distal end 94 of the body 25. The body comprises a proximal end 95. The body 25 has a spring bore and an adjuster bore contained within a section of the body 25. A spring bore is a channel that the spring moves in as the spring expands or contracts in an axial direction along the longitudinal axis of the body 25. The adjuster bore is a section that the adjuster 24 moves in as the adjuster 24 moves in an axial direction along the longitudinal axis of the body 25. The side body opening 69 comprises a cross sectional shape that allows for a length of the proximal end 34 of the gripping mechanism 21 to move outside of the side body opening 69. The front opening 93 comprises a cross sectional shape that allows for a length of the gripping mechanism 21 to be inserted into the body 25.

In a preferred embodiment of the present invention, the adjuster bore comprises a fastener that is used to engage the adjuster 24 to the body 25. In a preferred embodiment of the present invention, the adjuster bore comprises the fastener that has a plurality of threads. Other fasteners of the adjuster bore that could be used for engaging the adjuster 24 to the body 25 include, but are not limited to, adhesives, glues, rivets, blind fasteners, mechanical snaps and other mechanical fasteners. Those skilled in the art will recognize that other methods of engaging the adjuster 24 to the body 25 are known in the art and would be within the spirit and scope of the present invention.

In a preferred embodiment of the present invention, the body 25 comprises anodized aluminum. In another embodiment of the present invention, the body 25 comprises an anodized aluminum alloy. Those skilled in the art will recognize the body 25 can be made of many other materials and be within the spirit and scope of the present invention.

In a preferred embodiment of the present invention, the plurality of body openings 68 are approximately circular. In other embodiments of the present invention, the plurality of body openings 68 have a cross section that is square, rectangular, hexagonal, triangular, oval or similar shapes. Those skilled in the art will recognize the plurality of body openings 68 can be of many other shapes and be within the spirit and scope of the present invention.

Figure 5B:
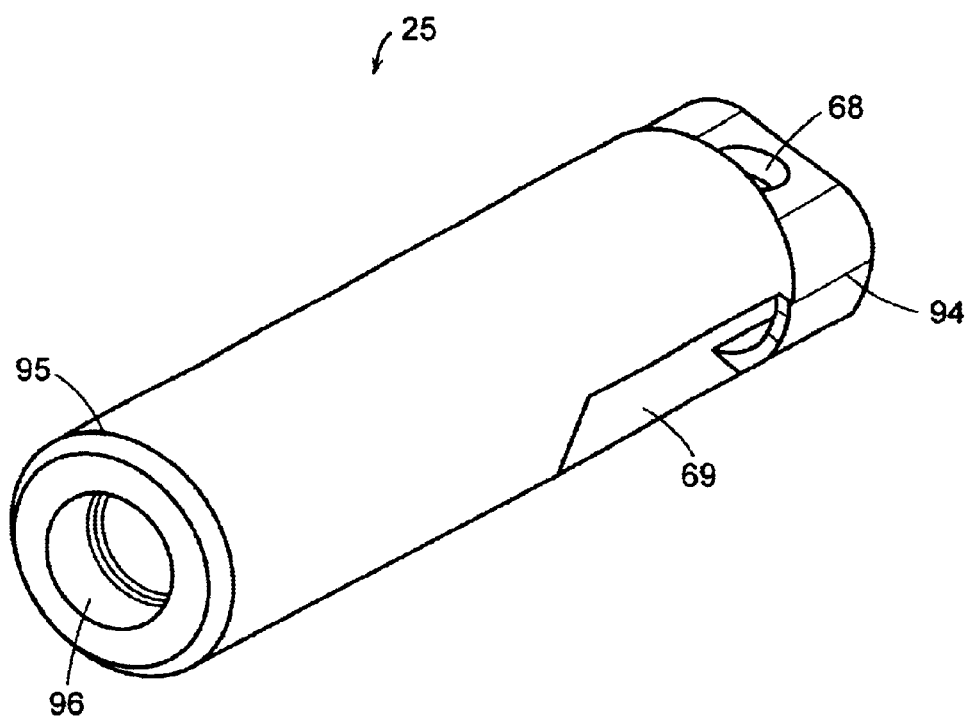
FIG. 5B shows a perspective view of the body of a torque limiting wrench of the present invention as seen from a proximal end.

FIG. 5B shows a perspective view of the body 25 of the present invention as seen from the proximal end 95. The body 25 comprises the side body opening 69 and the plurality of body openings 68 at the distal end 94 of the body 25. In a preferred embodiment of the present invention, a body cavity 96 is located at the proximal end 95 of the body 25. The body cavity 96 allows for ample space for a user to place an adjustment tool that engages the adjuster head 64 to move the adjuster head 64 in order to move the adjuster 24 in an axial direction along a longitudinal length of the adjuster bore. In a preferred embodiment of the present invention, the body cavity 96 is approximately circular. In other embodiments of the present invention, the body cavity 96 is square, rectangular, triangular, hexagonal, oval or similar shapes. Those skilled in the art will recognize the body cavity 96 can be of many other shapes and be within the spirit and scope of the present invention.

Figure 6:
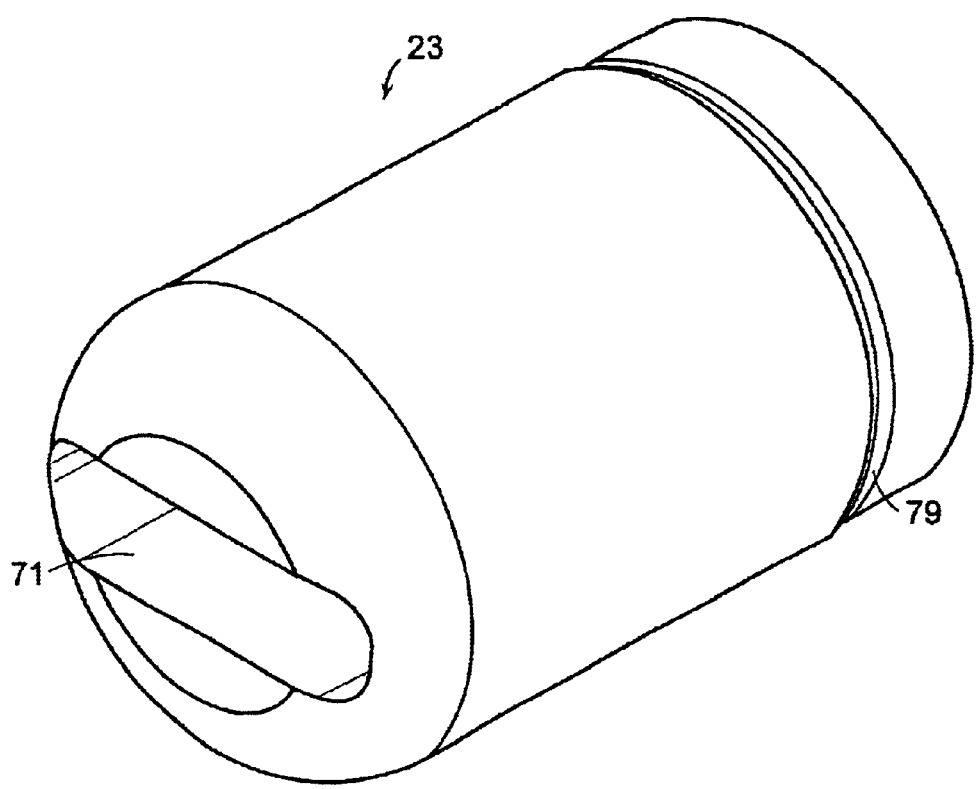
FIG. 6 shows a perspective view of a cap of a torque limiting wrench of the present invention.

FIG. 6 shows a perspective view of the cap 23 of the torque limiting wrench 20 of the present invention. The cap 23 is a component of the torque limiting assembly. In a preferred embodiment of the present invention, the cap 23 comprises a cap opening 71 along a length of the cap 23 and a cap fastener 79 that engages the cap 23 to the handle 22.

In a preferred embodiment of the present invention, the cap 23 comprises anodized aluminum. In another embodiment of the present invention, the cap 23 comprises an anodized aluminum alloy. Those skilled in the art will recognize the cap 23 can be made of many other materials and be within the spirit and scope of the present invention.

In a preferred embodiment of the present invention, the cap fastener 79 comprises a plurality of threads. Other cap fasteners 79 that could be used for engaging the cap 23 to the handle 22 include, but are not limited to, adhesives, glues, rivets, blind fasteners, mechanical snaps and other mechanical fasteners. Those skilled in the art will recognize that other methods of engaging the cap 23 to the handle 22 are known in the art and would be within the spirit and scope of the present invention.

Figure 7:
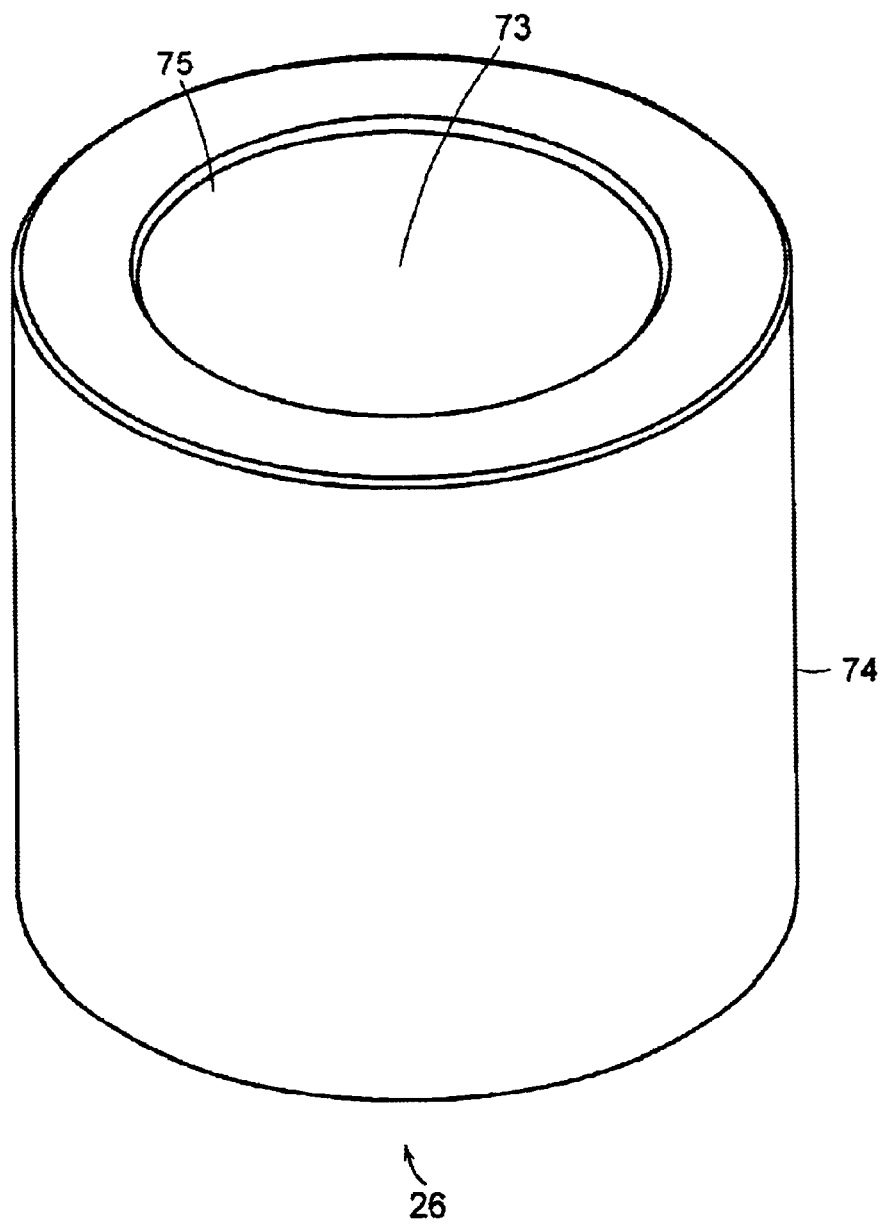
FIG. 7 shows a perspective view of a bushing of a torque limiting wrench of the present invention.

FIG. 7 shows a perspective view of a bushing 26 of the torque limiting wrench 20 of the present invention. The bushing 26 is an adapter that is used to constrain, guide or reduce friction. The bushing 26 comprises a bushing channel 73 through the bushing 26. In a preferred embodiment of the present invention, the bushing channel 73 is approximately circular. In an alternative embodiment of the present invention, the bushing channel 73 has a cross section that is square, rectangular, hexagonal, triangular, oval or similar cross sections. Those skilled in the art will recognize the bushing 26 can have a bushing channel 73 of many other shapes and be within the spirit and scope of the present invention.

The bushing 26 comprises a material that prevents galling between both an outside surface 74 and an inside surface 75 of the bushing 26. Galling is a condition in which an engaging surface between a first material and a second material becomes damaged. The damage results in limited movement of a first material relative to a second material. The bushing 26 comprises a material that prevents wear and tear of the outer surface 74 of the bushing 26 and the inner surface of the gripping mechanism opening 55. The bushing comprises a material that prevents wear and tear of the inner surface 75 of the bushing 26 and the pin 29. In an embodiment of the present invention, the inner surface 75 of the bushing 26 is lubricated. In a preferred embodiment of the present invention, the bushing 26 comprises rulon. Those skilled in the art will recognize the bushing 26 can be made of many other materials and be within the spirit and scope of the present invention.

In a preferred embodiment of the present invention, the bushing 26 comprises Rulon 641. Rulon is a specially compounded form of polytetrafluoroethylene (PTFE) and other inert ingredients. Rulon 641 is a white material that is known in the art to be used for food and drug contact bearing applications. Rulon 641 is a FDA cleared material that has excellent load and wear characteristics and a wide ranging temperature capability. Rulon 641 is compatible with stainless steel mating surfaces and is unaffected by all common acids, bases and solvents. Those skilled in the art will recognize that the bushing 26 could be composed of many other materials and be within the spirit and scope of the present invention.

Figure 8:
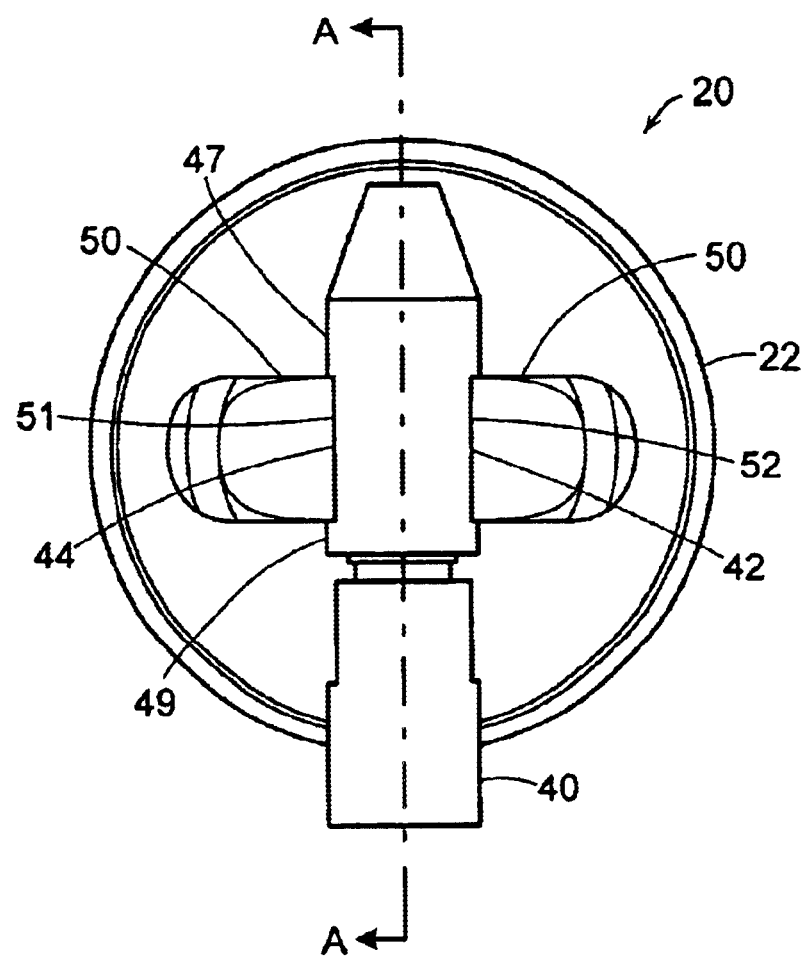
FIG. 8 shows a front end view of a torque limiting wrench of the present invention engaging a medical device.

FIG. 8 shows a front end view of the torque limiting wrench 20 of the present invention engaging the medical device 40 at an at least one predetermined location 42, 44 of the medical device 40. In an embodiment of the present invention, the torque limiting wrench 20 engages the medical device 40. In a preferred embodiment of the present invention, the pair of wrench flats 50 engages the medical device 40 at the predetermined locations 42, 44 of the medical device 40. In an embodiment of the present invention, the predetermined locations 42, 44 of the medical device 40 comprise a plurality of indents where the first jaw 51 and the second jaw 52 of the pair of wrench flats 50 engage the medical device 40. In a preferred embodiment of the present invention, the plurality of indents are approximately flat. Those skilled in the art will recognize the plurality of indents can be of many other shapes and be within the spirit and scope of the present invention.

In an embodiment of the present invention, the predetermined locations 42, 44 of the medical device 40 comprise the plurality of indents where the first jaw 51 engages the medical device 40. In another embodiment of the present invention, the predetermined locations 42, 44 of the medical device 40 comprise the plurality of indents where the second jaw 52 engages the medical device 40. In a preferred embodiment of the present invention, the pair of wrench flats 50 are placed onto the medical device 40 at the plurality of indents. In another embodiment of the present invention, the torque limiting wrench 20 engages the medical device 40 at non-predetermined locations. Those skilled in the art will recognize a torque limiting wrench 20 can engage a medical device 40 at a multitude of locations and be within the spirit and scope of the present invention.

In a preferred embodiment of the present invention, the opening distance between the pair of wrench flats 50 allows the pair of wrench flats 50 to be placed onto the medical device 40 at the plurality of indents at the predetermined locations 42, 44 of the medical device 40. In a preferred embodiment of the present invention, an opening distance between the pair of wrench flats 50 is set so the opening between the pair of wrench flats 50 is smaller than the outermost surface of the component of the medical device 40 to be tightened. An opening distance between the pair of wrench flats 50 that is smaller than the outermost surface of the component of the medical device 40 allows the pair of wrench flats 50 to be placed onto the medical device 40 at the predetermined locations 42, 44 rather than moving the pair of wrench flats along the longitudinal axis of the medical device 40 to the predetermined locations 42, 44. In a preferred embodiment, the opening distance between the pair of wrench flats 50 is set so the opening between the pair of wrench flats 50 is smaller than an at least one circumferential position of proximal sections 47, 49 of the medical device 40. An opening distance between the pair of wrench flats 50 that is smaller than an at least one circumferential position of proximal sections 47, 49 of the medical device 40 allows the pair of wrench flats 50 to be placed onto the medical device 40 at the predetermined locations 42, 44 rather than moving the pair of wrench flats along the longitudinal axis of the medical device 40 to the predetermined locations 42, 44. In a preferred embodiment of the present invention, the pair of wrench flats 50 can not be moved along the longitudinal axis of the medical device 40 along any circumferential position of proximal sections 47, 49 and to the predetermined locations 42, 44 of the medical device 40.

Figure 9:
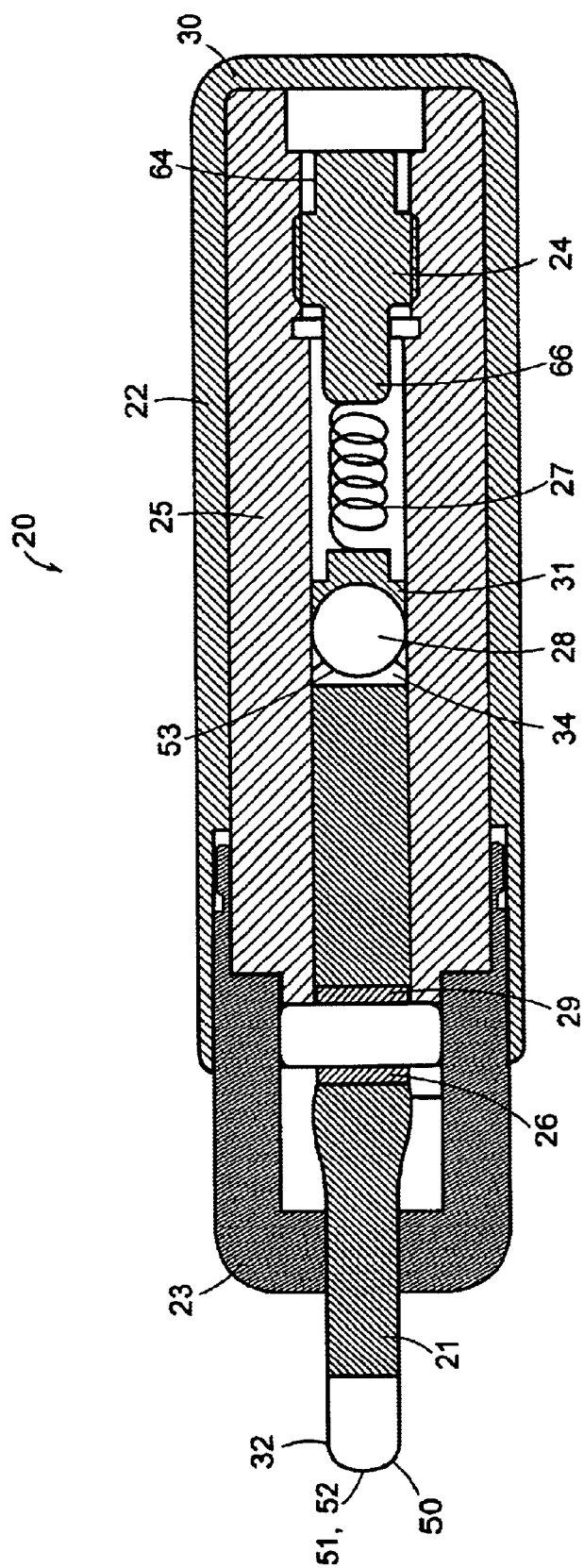
FIG. 9 shows a sectional view of the torque limiting wrench of the present invention as seen along line A—A of FIG. 8 without the medical device.

FIG. 9 shows a cross sectional view of the torque limiting wrench 20 of the present invention as seen from line A—A of FIG. 8. The torque limiting wrench 20 comprises the gripping mechanism 21, the handle 22 and the torque limiting assembly. The torque limiting assembly comprises the cap 23, the adjuster 24, the body 25, the bushing 26, the spring 27, the ball 28, the ball seat 31 and the pin 29. The cap 23 is engaged to the handle 22 for a length of the handle 22. The cap 23 surrounds a length of the gripping mechanism 21, the bushing 26, the pin 29 and a length of the body 25. The body 25 is enclosed within a length of the handle 22 and extends from the proximal end 30 of the torque limiting wrench 20 to a location of the gripping mechanism 21. The body 25 surrounds the adjuster 24, the bushing 26, the spring 27, the ball 28 and the pin 29. The torque limiting assembly is used in setting the predetermined torque of the torque limiting wrench 20. The predetermined torque is set by engaging an adjustment tool known in the art to the adjuster head 64 and moving the adjuster 24 in an axial direction along the longitudinal axis of the torque limiting wrench 20.

In an embodiment of the present invention shown in FIG. 9, the torque limiting wrench 20 of the present invention is in a neutral position. In the neutral position, there is no torque applied to the medical device 40. The neutral position can result when the pair of wrench flats 50 is placed over the medical device and no torque is applied to the medical device 40. The neutral position can also result when there is no part between the pair of wrench flats 50 and, as a result, no torque being applied by the pair of wrench flats 50. In the neutral position, the ball 28 fits into the detent 53 of the gripping mechanism 21 with the ball 28 contacting a portion of the detent 53 with an approximately equal force on the portions of the detent 53. The axial position of the gripping mechanism 21 is fixed by the pin 29. As a torque is transferred from the pair of wrench flats 50 to the medical device 40, the gripping mechanism 21 rotates around the pin 29.

The predetermined torque of the torque limiting wrench 20 is set by applying a force to the adjuster head 64 when the torque limiting wrench 20 is in a neutral position. In a preferred embodiment of the present invention, the handle 22 is disengaged from the cap 23 to expose the adjuster head 64. An adjustment tool capable of engaging the adjuster head 64 is used to apply a force to the adjuster head 64. Application of a force to the adjuster head 64 in one direction compresses the spring 27 against the ball seat 31 as the adjuster 24 moves in an axial direction toward the distal end 32 of the torque limiting wrench 20. With the gripping mechanism 21 in a fixed position, the ball 28 rests in a fixed position inside a portion of the detent 53 and the ball seat 31. The length of the spring 27 decreases in the length between the distal end 66 of the adjuster 24 and the ball seat 31. A decreased length of the spring 27 allows for a larger predetermined torque to be set. Application of a force to the adjuster head 64 in an opposite direction allows the spring 27 to extend as the adjuster 24 moves in an axial direction toward the proximal end 30 of the torque limiting wrench 20. With the gripping mechanism 21 in a fixed position, the ball 28 rests in an approximately fixed position between a portion of the detent 53 and the ball seat 31. The length of the spring 27 increases in the length between the distal end 66 of the adjuster 24 and the ball 28. An increased length of the spring 27 allows for a smaller predetermined torque to be set. The predetermined torque is set with a calibrated gauge offline to a value that is chosen by a user for a specific application. The axial position of the adjuster 24 is set by applying a force to the adjuster head 64 to move the spring 27 in an axial direction along a length of the wrench 20 and the predetermined torque is checked against the calibrated gauge.

In a preferred embodiment of the present invention, the predetermined torque is about 25 inch-pounds. In another embodiment of the present invention, the predetermined torque varies between about 23 inch-pounds and about 27 inch-pounds. Those skilled in the art will recognize a torque limiting wrench 20 can be set at a predetermined torque smaller than about 23 inch-pounds and larger than about 27 inch-pounds and be within the spirit and scope of the present invention.

In an embodiment of the present invention, the pair of wrench flats 50 engage the medical device 40 in a manner that the first jaw 51 and the second jaw 52 engage the medical device 40 at a predetermined location of the medical device 40. The first jaw 51 of the pair of wrench flats 50 engages the medical device 40 to move a component of the medical device 40 to tighten the medical device 40. As the force is being applied to the handle 22 to move a component of the medical device 40, the gripping mechanism 21 pivots around the pin 29. As a user continues application of a force to the handle 22, the gripping mechanism 21 pivots around the pin 29, until the applied force produces a slip condition. The slip condition refers to a condition when the ball 28 pushes the ball seat 31 against the spring 27 and the ball 28 moves out of the neutral position in the detent 53 and moves along a portion of the detent 53 to the first endface 91 or the second endface 92 at the proximal end 34 of the gripping mechanism 21. The slip condition is an indicator that the predetermined torque has been reached. The slip condition corresponds to the ball 28 moving out of the detent 53 and to the first endface 91 at the proximal end 34 of the gripping mechanism 21. The slip condition corresponds to the ball 28 moving out of the detent 53 and to the second endface 92 at the proximal end 34 of the gripping mechanism 21. In a preferred embodiment of the present invention, a section at the proximal end 34 of the gripping mechanism 21 makes contact with an inner surface of the body 25. In another embodiment of the present invention, a section of the gripping mechanism 21 between the distal end 97 and proximal end 34 of the gripping mechanism 21 makes contact with the cap 23. When the predetermined torque is reached, an indicator is made to indicate the predetermined torque has been reached. In a preferred embodiment of the present invention, there is an audible and tactile indicator when the predetermined torque is reached. In a preferred embodiment of the present invention, the audible indicator is a sound.

In a preferred embodiment of the present invention, there is an audible indicator and a tactile indicator when the predetermined torque is reached. In another embodiment of the present invention, there is the audible indicator only. In another embodiment of the present invention, there is the tactile indicator only. The audible indicator is a distinctive sound when the predetermined torque is reached. In a preferred embodiment of the invention, the audible indicator is a clicking sound. Those skilled in the art will recognize that other audible indicators are within the spirit and scope of the present invention. The tactile indicator is a distinctive indicator a user feels when the wrench slips. Those skilled in the art will recognize that other tactile indicators are within the spirit and scope of the present invention. Those skilled in the art will also recognize the indicator can be the audible indicator, the tactile indicator or both the audible indicator and the tactile indicator and be within the spirit and scope of the present invention.

In another embodiment of the present invention, the pair of wrench flats 50 engage the medical device 40 in a manner that a second jaw 52 of the pair of wrench flats 50 engages the medical device 40 as a force is applied to the handle 22 and transmitted to the second jaw 52 and to the medical device 40.

In a preferred embodiment of the present invention, the ball seat 31 comprises a low friction material that allows the ball 28 to move around and rotate within the ball seat 31. In a preferred embodiment of the present invention, the ball seat 31 comprises teflon (polytetrafluoroethylene). Teflon is a tough, flexible and chemically inert material that has a low coefficient of friction which makes it a slippery material. Teflon is heat resistant and will not absorb moisture or rust, even when subjected to harsh environments. Those skilled in the art will recognize that the ball seat 31 can be comprised of many other materials having a low coefficient of friction and be within the spirit and scope of the present invention.

In a preferred embodiment of the present invention, the ball 28 comprises a material that is tough and will not affect the surface conditions of a part that it engages to. In a preferred embodiment of the present invention, the ball 28 comprises stainless steel. Those skilled in the art will recognize a ball 28 can be made of many other materials and be within the spirit and scope of the present invention.

In a preferred embodiment of the present invention, the spring 27 comprises a material that is tough and will not affect the surface conditions of the part it engages to. In a preferred embodiment of the present invention, the spring 27 comprises stainless steel. Those skilled in the art will recognize the spring 27 can be made of many other materials and be within the spirit and scope of the present invention.

In a preferred embodiment of the present invention, the pin 29 comprises a material that is tough and will not affect the surface conditions of the part it engages to. In a preferred embodiment of the present invention, the pin 29 comprises stainless steel. Those skilled in the art will recognize the pin 29 can be made of many other materials and be within the spirit and scope of the present invention.

In a preferred embodiment of the present invention, all components of the torque limiting wrench 20 comprise a material that allows for the torque limiting wrench 20 to undergo a sterilization process. In a preferred embodiment of the present invention, the torque limiting wrench 20 is composed of materials that allow the torque limiting wrench 20 to undergo an autoclave operation. An autoclave is a machine that sterilizes instruments or materials with high pressure or heat or pressurized steam. An autoclave kills biological contamination and denaturing proteins and will not remove chemical contamination. Those skilled in the art will recognize that the torque limiting wrench 20 of the present invention could undergo many other sterilization processes that are within the spirit and scope of the present invention.

The present invention also provides a method of transferring a torque from a torque limiting wrench to a medical device wherein the torque limiting wrench provides an indicator when the predetermined torque is reached so as not to affect an at least one acoustic property of the medical device. The method of transferring the torque comprises setting a predetermined torque on the torque limiting wrench using an adjuster, engaging a pair of wrench flats of a gripping mechanism of the torque limiting wrench to the medical device and applying a force from a handle of the torque limiting wrench to the medical device using the gripping mechanism.

A force applied to the handle of the gripping mechanism results in a torque applied to the medical device. The torque applied to the medical device tightens the medical device until the predetermined torque is reached. When the predetermined torque is reached, the user will feel the tactile indicator as the torque limiting wrench slips. In addition, when the predetermined torque is reached, the audible indicator makes a sound. The torque limiting wrench slips when the predetermined torque is reached.

Use of a torque limiting wrench 20 of the present invention comprises a plurality of steps. A user sets a predetermined torque of the torque limiting wrench 20 by engaging the adjustment tool to the adjuster head 64 and moving the adjuster 24 along the longitudinal axis of the torque limiting wrench 20. The pair of wrench flats 50 of the gripping mechanism 21 of the torque limiting wrench 20 is placed onto the predetermined locations 42, 44 of the medical device 40. The user applies a force to the handle 22 to engage the pair of wrench flats 50 to the medical device 40, transmitting a torque to the medical device 40. As the torque to the medical device 40 is increased by an increased force to the handle 22, the gripping mechanism 21 pivots around the pin 29 and the ball 28 pushes the ball seat 31 against the spring 27 and the ball 28 moves out of a neutral position in the detent 53. When the predetermined torque is reached, a slip condition results as the ball 28 moves out of the detent 53 and contacts the first endface 91 or the second endface 92 at the proximal end 34 of the gripping mechanism 21. The torque limiting wrench 20 produces the audible indicator and the tactile indicator as the predetermined torque is reached.

The present invention provides an apparatus and method of transferring a torque from a torque limiting wrench to a medical device wherein the torque limiting wrench is set to a predetermined torque. The torque limiting wrench is set to a predetermined torque to provide a plurality of indicators which indicate the predetermined torque has been reached in order to prevent adverse affects of the medical device including damage to the medical device and detrimental effects to the acoustic characteristics of the medical device.

All patents, patent applications, and published references cited herein are hereby incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A torque limiting wrench comprising:
   a gripping mechanism comprising a proximal end having a detent for engaging a ball, a distal end terminating in a pair of wrench flats, and an opening between the proximal end and the distal end of the gripping mechanism;
   a handle extending from the gripping mechanism;
   a body contained within the handle and engaged to the gripping mechanism by a pin extending through a plurality of body openings in the body and a bushing located in an opening of the gripping mechanism:
   a torque limiting assembly located within the handle, the torque limiting assembly comprising a spring and a movable adjuster located at a proximal end of the handle to change a length of the spring located between the movable adjuster and the proximal end of the gripping mechanism for setting a predetermined torque; and
   the ball located between the detent and a ball seat engaging a distal end of the spring.

2. The torque limiting wrench of claim 1 wherein the gripping mechanism comprises the pair of wrench flats having a first jaw and a second jaw.

3. The torque limiting wrench of claim 1 wherein a shape of the detent allows the ball of the torque limiting assembly to travel along an inner surface of the detent and slip when the predetermined torque is reached.

4. The torque limiting wrench of claim 1 wherein the torque limiting assembly further comprises a cap engaging a distal end of the handle, the cap surrounding a length of the gripping mechanism.

5. The torque limiting wrench of claim 1 wherein the adjuster comprises an adjuster head at a proximal end of the adjuster.

6. The torque limiting wrench of claim 5, wherein the adjuster head allows the adjuster to be moved to apply a varying force to a spring for setting the predetermined torque.

7. The torque limiting wrench of claim 1 wherein the adjuster comprises a boss at a distal end of the adjuster.

8. The torque limiting wrench of claim 1 wherein the torque limiting wrench comprises a material that can undergo a sterilization process.

9. The torque limiting wrench of claim 1 wherein the torque limiting wrench comprises a material that can undergo an autoclave operation.

10. The torque limiting wrench of claim 1 wherein the predetermined torque is set by a predetermined axial location of the adjuster.

11. The torque limiting wrench of claim 1 wherein the torque limiting wrench produces an audible indicator when the predetermined torque is reached.

12. The torque limiting wrench of claim 1 wherein the torque limiting wrench produces a tactile indicator when the predetermined torque is reached.

13. The torque limiting wrench of claim 1 wherein the torque limiting wrench produces an audible and a tactile indicator when the predetermined torque is reached.

14. A torque limiting wrench for use with an ultrasonic medical device comprising:
    a gripping mechanism comprising a proximal end having a detent for engaging a ball and a distal end terminating in a pair of wrench flats;
    a handle extending from the gripping mechanism;
    a body contained within the handle and engaged to the gripping mechanism by a pin extending through a plurality of body opening in the body and a bushing located in an opening of the gripping mechanism;
    a torque limiting assembly located within the handle, the torque limiting assembly comprising a movable adjuster located at a proximal end of the handle to change a length of a spring located between the movable adjuster and the proximal end of the gripping mechanism for setting a predetermined torque; and
    the ball located between the detent and a ball seat engaging a distal end of the spring,
    wherein the torque limiting wrench applies the predetermined torque to the ultrasonic medical device without damaging the ultrasonic medical device.

15. The torque limiting wrench of claim 14 wherein an application of a force to the handle of the torque limiting wrench is transmitted to a torque applied by the pair of wrench flats of the gripping mechanism to move a component of the ultrasonic medical device until a predetermined torque is reached.

16. The torque limiting wrench of claim 14 wherein a first jaw and a second jaw of the pair of wrench flats of the gripping mechanism engages the ultrasonic medical device.

17. The torque limiting wrench of claim 14 wherein the gripping mechanism comprises a material that will not damage a surface of the ultrasonic medical device.

18. The torque limiting wrench of claim 14 wherein the torque limiting wrench slips when a force applied to the handle reaches the predetermined torque.

19. The torque limiting wrench of claim 14 wherein the torque limiting wrench produces an audible indicator when the predetermined torque is reached.

20. The torque limiting wrench of claim 14 wherein the torque limiting wrench produces a tactile indicator when the predetermined torque is reached.

21. The torque limiting wrench of claim 14 wherein the torque limiting wrench produces an audible indicator and a tactile indicator when the predetermined torque is reached.

22. The torque limiting wrench of claim 14 wherein the torque limiting wrench comprises a material that can undergo a sterilization process.

23. The torque limiting wrench of claim 14 wherein the torque limiting wrench comprises a material that can undergo an autoclave operation.

24. The torque limiting wrench of claim 14 wherein a predetermined torque is set by a predetermined axial location of the movable adjuster of the torque limiting assembly.

25. The torque limiting wrench of claim 1 further comprising a handle opening at a proximal end of the handle for accessing the movable adjuster.

26. The torque limiting wrench of claim 1 wherein the movable adjuster is accessed without removing the handle of the torque limiting wrench.

27. The torque limiting wrench of claim 1 wherein a distance between a first jaw and a second jaw of the pair of wrench flats is designed to fit onto the medical device.

28. The torque limiting wrench of claim 1 wherein the handle comprises a surface finish having a non-slip grip.

29. The torque limiting wrench of claim 14 further comprising a handle opening at a proximal end of the handle for accessing a movable adjuster.

30. The torque limiting wrench of claim 14 wherein a movable adjuster is accessed without removing the handle of the torque limiting wrench.

31. The torque limiting wrench of claim 14 wherein a distance between a first jaw and a second jaw of the pair of wrench flats is designed to fit onto the ultrasonic medical device.

32. The torque limiting wrench of claim 14 wherein the handle comprises a surface finish having a non-slip grip.

33. A torque limiting wrench for applying a predetermined torque to an ultrasonic medical device without damaging the ultrasonic medical device comprising:

a pair of wrench flats extending from a distal end of a gripping mechanism;

a detent in a proximal end of the gripping mechanism for engaging a ball;

a handle having a non-slip grip extending from the gripping mechanism;

a body contained within the handle and engaged to the gripping mechanism by a pin extending through a plurality of body openings in the body and a bushing located in an opening of the gripping mechanism;

a torque limiting assembly located within the handle, the torque limiting assembly comprising a movable adjuster located at a proximal end of the handle to change a length of a spring located between the movable adjuster and the proximal end of the gripping mechanism for setting the predetermined torque; and the ball located between the detent and a ball seat engaging a distal end of the spring, wherein the movable adjuster is accessed through a handle opening at a proximal end of the handle without removing the handle of the torque limiting wrench.

34. The torque limiting wrench of claim 33 wherein an application of a force to the handle of the torque limiting wrench is transmitted as a torque applied by the pair of wrench flats of the gripping mechanism to move a component of the ultrasonic medical device until a predetermined torque is reached.

35. The torque limiting wrench of claim 33 wherein a first jaw and a second jaw of the pair of wrench flats of the gripping mechanism engages the ultrasonic medical device.

36. The torque limiting wrench of claim 33 wherein the gripping mechanism comprises a material that will not damage a surface of the ultrasonic medical device.

37. The torque limiting wrench of claim 33 wherein the torque limiting wrench slips when a force applied to the handle reaches the predetermined torque.

38. The torque limiting wrench of claim 33 wherein the torque limiting wrench produces an audible indicator when the predetermined torque is reached.

39. The torque limiting wrench of claim 33 wherein the torque limiting wrench produces a tactile indicator when the predetermined torque is reached.

40. The torque limiting wrench of claim 33 wherein the torque limiting wrench produces an audible indicator and a tactile indicator when the predetermined torque is reached.

41. The torque limiting wrench of claim 33 wherein the torque limiting wrench comprises a material that can undergo a sterilization process.

42. The torque limiting wrench of claim 33 wherein the torque limiting wrench comprises a material that can undergo an autoclave operation.

43. The torque limiting wrench of claim 33 wherein a predetermined torque is set by a predetermined axial location of the movable adjuster of the torque limiting assembly.

* * * * *

UNITED STATES PATENT AND TRADEMARK OFFICE
CERTIFICATE OF CORRECTION

PATENT NO.      : 6,807,885 B2                                                Page 1 of 1
DATED           : October 26, 2004
INVENTOR(S)     : Loper, James H.

It is certified that error appears in the above-identified patent and that said Letters Patent is hereby corrected as shown below:

Column 15,
Line 37, the punctuation after the third limitation should be a semi-colon -- ; -- instead of a colon ":".

Column 16,
Line 27, the word "opening" should be plural so it reads -- openings --.

Signed and Sealed this

Seventeenth Day of May, 2005

JON W. DUDAS
*Director of the United States Patent and Trademark Office*